(12) United States Patent
Coale et al.

(10) Patent No.: US 9,788,951 B2
(45) Date of Patent: Oct. 17, 2017

(54) SHAPEABLE POROUS METAL IMPLANT

(71) Applicant: Zimmer, Inc., Warsaw, IN (US)

(72) Inventors: Bradford J. Coale, Chester, NJ (US); Steven Seelman, Montclair, NJ (US)

(73) Assignee: Zimmer, Inc., Warsaw, IN (US)

( * ) Notice: Subject to any disclaimer, the term of this patent is extended or adjusted under 35 U.S.C. 154(b) by 26 days.

(21) Appl. No.: 14/845,471

(22) Filed: Sep. 4, 2015

(65) Prior Publication Data

US 2016/0074166 A1    Mar. 17, 2016

Related U.S. Application Data

(60) Provisional application No. 62/049,486, filed on Sep. 12, 2014.

(51) Int. Cl.

| | |
|---|---|
| *A61F 2/28* | (2006.01) |
| *A61L 27/04* | (2006.01) |
| *A61L 27/56* | (2006.01) |
| *A61B 17/70* | (2006.01) |
| *A61B 17/80* | (2006.01) |
| *A61F 2/30* | (2006.01) |

(52) U.S. Cl.
CPC ........... *A61F 2/2846* (2013.01); *A61B 17/70* (2013.01); *A61B 17/8085* (2013.01); *A61L 27/047* (2013.01); *A61L 27/56* (2013.01); *A61F 2002/3092* (2013.01); *A61F 2002/30265* (2013.01); *A61F 2002/30298* (2013.01); *A61F 2002/30576* (2013.01); *A61F 2002/30772* (2013.01); *A61L 2430/02* (2013.01)

(58) Field of Classification Search
CPC .. A61F 2/30; A61F 2/3067; A61F 2/28; A61F 2/2846
See application file for complete search history.

(56) References Cited

U.S. PATENT DOCUMENTS

| | | | |
|---|---|---|---|
| 4,693,721 A * | 9/1987 | Ducheyne | ........... A61F 2/30907 419/24 |
| 5,282,861 A | 2/1994 | Kaplan | |
| 6,837,891 B2 | 1/2005 | Davison et al. | |
| 7,001,397 B2 | 2/2006 | Davison et al. | |
| 7,033,369 B2 | 4/2006 | Davison et al. | |
| 7,108,705 B2 | 9/2006 | Davison et al. | |
| 7,223,278 B2 | 5/2007 | Davison et al. | |
| 7,670,354 B2 | 3/2010 | Davison et al. | |
| 7,674,273 B2 | 3/2010 | Davison et al. | |

(Continued)

OTHER PUBLICATIONS

Levine, Brett R, et al., "Experimental and clinical performance of porous tantalum in orthopedic surgery", Biomaterials, (27), (Sep. 2006), 4671-81.

*Primary Examiner* — Jason-Dennis Stewart
(74) *Attorney, Agent, or Firm* — Schwegman Lundberg & Woessner, P.A.

(57) ABSTRACT

Shapeable porous metal implants and methods for use in various procedures are disclosed. The implants can comprise a shell according to some examples. According to one example, the method can include providing a sheet of highly porous metal material having a porosity of between 55% and 90%, and wrapping the sheet of highly porous metal material around at least a first bone of the patient. Further examples can form the sheet intra-operatively to a desired shape. In an example, the porous metal sheet can be formed of tantalum or tantalum alloys.

17 Claims, 6 Drawing Sheets

(56) References Cited

U.S. PATENT DOCUMENTS

| | | |
|---|---|---|
| 7,892,171 B2 | 2/2011 | Davison et al. |
| 7,892,249 B2 | 2/2011 | Davison et al. |
| 7,918,382 B2 | 4/2011 | Charlebois et al. |
| 7,985,237 B2 | 7/2011 | Davison et al. |
| 8,317,817 B2 | 11/2012 | Davison et al. |
| 8,540,746 B2 | 9/2013 | Davison et al. |
| 8,608,049 B2 | 12/2013 | Hippensteel et al. |
| 2004/0254630 A1 * | 12/2004 | Yang .................. A61F 2/91 623/1.15 |
| 2012/0125896 A1 | 5/2012 | Vargas et al. |
| 2013/0178947 A1 * | 7/2013 | Monaghan .............. A61L 27/56 623/23.55 |
| 2013/0282140 A1 * | 10/2013 | Ringeisen .............. A61B 17/80 623/23.72 |

\* cited by examiner

SHAPEABLE POROUS METAL IMPLANT

CLAIM OF PRIORITY

This application claims the benefit of U.S. Provisional Patent Application Ser. No. 62/049,486, filed on Sep. 12, 2014, the benefit of priority of which is claimed hereby, and which is incorporated by reference herein in its entirety.

TECHNICAL FIELD

The present application relates to orthopedic prostheses, and more particularly, to an intra-operatively shapeable porous implant and methods of using the same.

BACKGROUND

Orthopedic procedures are commonly utilized to repair and/or replace damaged bone and tissue in the human body. Such procedures can utilize orthopedic implants to replace or augment body components or portions of body components that cannot be regenerated or are no longer functioning properly. Examples of orthopedic implants include spinal implants, dental implants, artificial knees, hips, and ankle joints.

Some orthopedic implants and/or procedures can utilize materials to provide structural support to an orthopedic implant, to fill a void in bone reconstruction or joint repair, to provide a structure for permitting ingrowth and attachment of tissue, etc. Such materials can be used to provide structural support to a patient's tissue, such as bone tissue. Among the materials that have been utilized for bone repair or reconstruction is a bone graft, which is known to provide support, promote healing, fill bony cavities, promote fusion and stabilize the sites of fractures.

OVERVIEW

The present inventors recognize, among other things, an opportunity to utilize a thin shapeable porous metal to intra-operatively mold or otherwise be shaped to a patient's anatomy and provide support to bone to aid in bone fusion, bone graft containment, to retain bone fragments and/or to direct bone growth, etc. The implant described herein can be used with various procedures to treat injuries such as a long bone fracture, a spinal injury, a maxiofacial injury, etc. In some cases, the implant described herein can be used to treat anatomy where bone injury has not occurred but the risk of a bone injury is present due to osteoporosis and other forms of bone degeneration.

To further illustrate the shapeable porous implant and methods disclosed herein, a non-limiting list of examples is provided here:

In Example 1, a method of supporting bone in a patient, the method can optionally include providing a sheet of highly porous metal material having a porosity of between 55% and 90% for encouraging bone ingrowth into said sheet, and wrapping the sheet around at least a first bone of the patient.

In Example 2, the method of any one or any combination of Examples 1-11 can optionally have the wrapping include shaping the sheet intra-operatively to a desired shape to match an anatomy of the patient.

In Example 3, the method of any one or any combination of Examples 1-11 wherein the sheet can optionally have a thickness of between about 0.02 inch and about 0.07 inch.

In Example 4, the method of any one or any combination of Examples 1-11 wherein the sheet can optionally be introduced as a roll to an operative site adjacent the first bone.

In Example 5, the method of any one or any combination of Examples 1-11 can further optionally include wrapping the sheet around a second bone for fusing the first bone to the second bone.

In Example 6, the method of any one or any combination of Examples 1-11 wherein the wrapping can optionally include shaping the sheet in vivo to an anatomy of the patient.

In Example, 7, the method of any one or any combination of Examples 1-11 wherein the method optionally treats one or more of a long bone fracture, a spinal injury, and a maxiofacial injury.

In Example 8, the method of any one or any combination of Examples 1-11 can further optionally include disposing the sheet to interface with multiple sides of the first bone to aid in the retention of bone fragments or to aid in directing bone growth.

In Example 9, the method of any one or any combination of Examples 1-11 wherein the sheet can optionally be wrapped fully around the first bone.

In Example 10, the method of any one or any combination of Examples 1-11 wherein wrapping the sheet can optionally configure the sheet as a bone grafting platform.

In Example 11, the method of any one or any combination of Examples 1-11 wherein the sheet can optionally have one or more features that are configured to facilitate retention of the sheet to the first bone of the patient.

In Example 12, an orthopedic implant, the implant can optionally include an implantable sheet having a first face opposite a second face, at least one of the first face and the second face comprising a tissue interfacing surface, the sheet can be formed of a highly porous metal material having a porosity of between 55% and 90%, wherein the tissue interface surface can include one or more features configured to facilitate retention of the sheet to an anatomy of a patient.

In Example 13, the implant of any one or any combination of Examples 12-18 wherein the sheet can optionally have a thickness of between about 0.02 inch and about 0.07 inch and is configured to allow the sheet to be molded intra-operatively to a desired shape.

In Example 14, the implant of any one or any combination of Examples 12-18 further comprising in combination with a surgical instrument adapted to receive the sheet as a roll for delivery to the patient.

In Example 15, the implant of any one or any combination of Examples 12-18 wherein the porous metal material can optionally comprise a tantalum or tantalum alloy.

In Example 16, the implant of any one or any combination of Examples 12-18 wherein the sheet can optionally be moldable to at least one bone for treatment of one or more of a long bone fracture, a spinal injury, and a maxiofacial injury.

In Example 17, the implant of any one or any combination of Examples 12-18 wherein the one or more features can optionally comprise a surface feature and/or an edge feature.

In Example 18, the implant of any one or any combination of Examples 12-18 wherein the one or more features can optionally comprise one or more of hooks, tabs, barbs, holes, and slots.

In Example 19, a method of fusing at least a first bone to a second bone, the method can optionally include providing a sheet of highly porous metal material having a porosity of between 55% and 90%, and positioning the sheet in contact with the first bone and the second bone for fusing the first bone to the second bone.

In Example 20, the method of any one or any combination of Examples 19-24 further optionally including molding the sheet intra-operatively to a desired shape.

In Example 21, the method of any one or any combination of Examples 19-24 wherein the positioning can optionally include wrapping the sheet around at least the first bone.

In Example 22, the method of any one or any combination of Examples 19-24 wherein the sheet can optionally be wrapped fully around the first bone.

In Example 23, the method of any one or any combination of Examples 19-24 wherein the first bone and the second bone can optionally comprise vertebras of a patient.

In Example 24, the method of any one or any combination of Examples 19-24 wherein the first bone and the second bone can optionally be part of a joint in a patient.

In Example 25, the implant or method of any one or any combination of Examples 1-24 can optionally be configured such that all elements or options recited are available to use or select from.

These and other examples and features of the present systems and methods will be set forth in part in the following Detailed Description. This Overview is intended to provide non-limiting examples of the present subject matter—it is not intended to provide an exclusive or exhaustive explanation. The Detailed Description below is included to provide further information about the present apparatus, systems and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present application relates to devices and methods for use in various procedures such as spinal fusion, long bone fracture, maxiofacial reconstruction, etc. In some instances, the shapeable porous implant can be shaped intra-operatively to mold with a patient's anatomy. The shaping of the device can occur in vivo. In further examples, the shapeable porous implant can be configured as a malleable sheet of highly porous material. The sheet can be wrapped to anatomical structures and/or defects such as posterior lateral gutters, transverse process, bone grafts, fusion across a joint (e.g., arthrodesis), etc. In some instances, the shapeable porous sheet can have features that aid with engagement to the patient's anatomy. The porous structure of the sheet promotes bone regrowth and/or ingrowth allowing the device to act as a fusion aid. Additionally or alternatively, the shapeable sheet can be used to treat a long bone fracture to retain bone fragments and/or help direct bone regrowth to a surgical site.

Figures 1A, 1B:
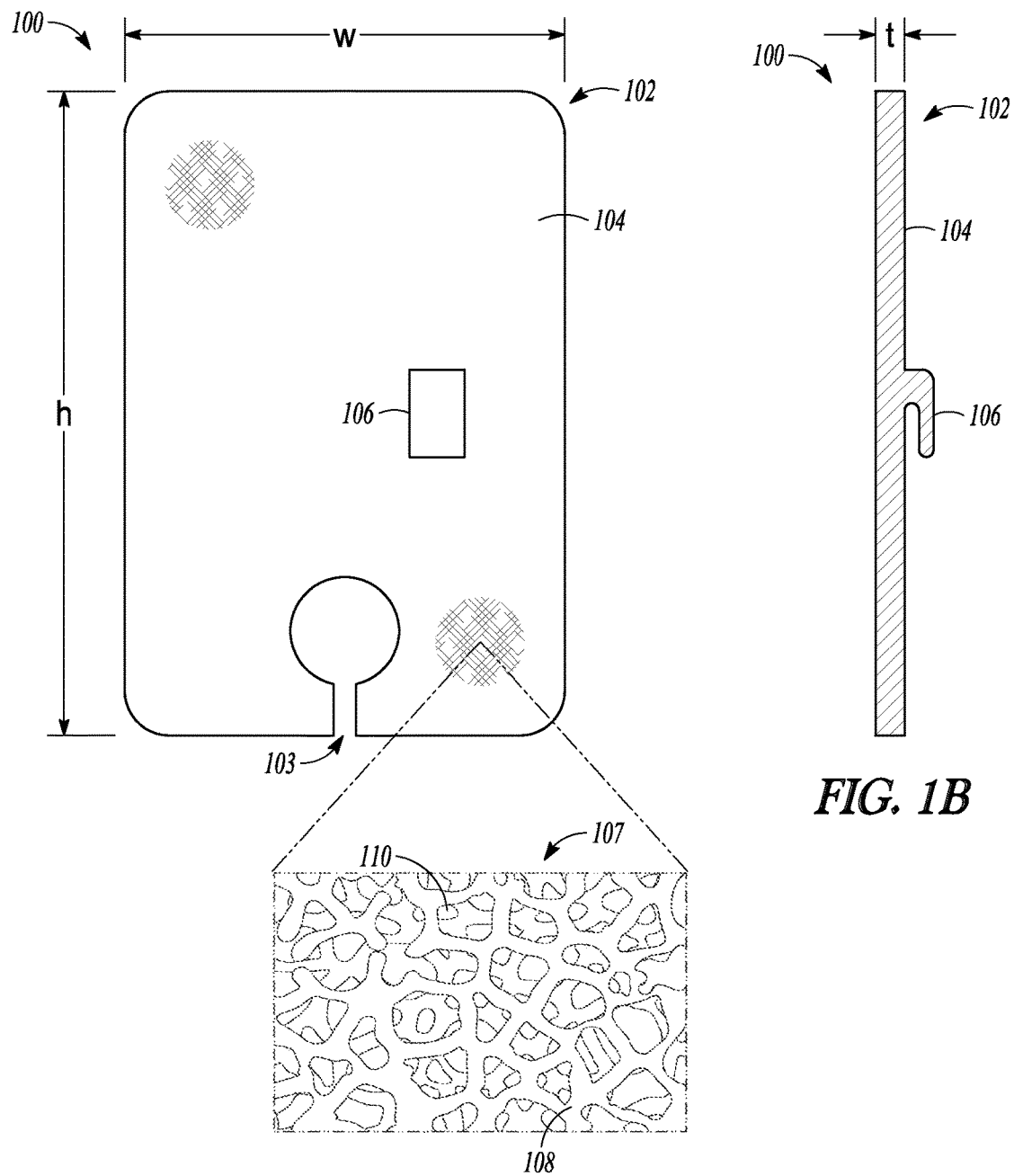
FIG. 1A is a plan view of a surface of a shapeable porous implant including an enlargement of the surface according to an example of the present application.
FIG. 1B is a side view of the shapeable porous implant of FIG. 1A.

FIGS. 1A and 1B illustrate an exemplary configuration of shapeable porous implant 100. As illustrated in FIGS. 1A and 1B, the shapeable porous implant 100 can comprise a sheet 102 of highly porous metal material having a width w, height h, and thickness t. The porosity of the highly porous metal material can be between 55% and 90%. A size and dimensions of the shapeable porous implant can be determined based, in part, on the size of additional implants (e.g., bone grafts), the porosity of the porous structure utilized, and/or the patient's anatomy, as described below.

In FIG. 1A, the sheet 102 can include one or more features 103, 106 disposed along a tissue interfacing surface 104. Edge features 103 such as slots, tabs, hooks, barbs, holes, etc. can extend from an interior portion of the sheet 102 toward the edges thereof. Surface feature 106 can also comprise slots, tabs, hooks, barbs, holes, etc. and can be disposed on the interior of the sheet 102. The one or more features 103, 106 can be configured to facilitate retention of the porous implant 100 to the anatomy of the patient and/or another implant. For example, a slot may receive a portion of a patient's bone or soft tissue. Similarly, a hook or barb can couple to a patient's bone or soft tissue. A hole can be adapted to receive a bone screw, suture, etc.

FIG. 1B illustrates a side view of the sheet 102 showing the tissue interfacing surface 104 and an example of the surface feature 106. In the example of FIG. 1B, the surface feature 106 can comprise a thickened region such as a hook. FIG. 1B illustrates that the thickness t of the sheet 102 can have a much smaller dimension than the width w and the height h. In some examples, the thickness t can be between about 0.02 inch to 0.07 inch. This thickness t (among other factors including porosity) allows the sheet 102 to be molded intra-operatively to a desired shape to wrap an anatomy of the patient as will be further discussed herein.

In an example, the shapeable porous implant 100 and sheet 102 can be formed of a metal or metal alloy having a porous structure, such as a porous metal described below, to facilitate bone ingrowth or regrowth (e.g., act as a fusion and healing aid).

The enlargement of FIG. 1A illustrates such a porous metal 107. The porous metal 107 includes a plurality of ligaments 108 defining a plurality of highly interconnected, three-dimensional open spaces or pores 110 therebetween. The porous metal structure can incorporate one or more of a variety of biocompatible metals. Such structures are particularly suited for contacting bone and soft tissue, and in this regard, can be useful as a bone substitute and as cell and tissue receptive material, for example, by allowing tissue to grow into the porous structure over time to enhance fixation (e.g., osseointegration) between the structure and surrounding bodily structures. According to certain examples of the present disclosure, an open porous metal structure may have a porosity as low as 55%, 65%, or 75% or as high as 80%, 85%, or 90%, or within any range defined between any pair of the foregoing values. An example of an open porous metal structure is produced using Trabecular Metal™ Technology available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference. In addition to tantalum, other biocompatible metals may also be used in the formation of a highly porous metal structure such as titanium, a titanium alloy, cobalt chromium, cobalt chromium molybdenum, tantalum, a tantalum alloy, niobium, or alloys of tantalum and niobium with one another or with other metals. It is also within the scope of the present disclosure for a porous metal structure to be in the form of a fiber metal pad or a sintered metal layer, such as a Cancellous-Structured Titanium™ (CSTi™) layer. CSTi™ porous layers are manufactured by Zimmer, Inc., of Warsaw, Ind. Cancellous-Structured Titanium™ and CSTi™ are trademarks of Zimmer, Inc.

Generally, a highly porous metal structure will include a large plurality of metallic ligaments defining open voids (e.g., pores) or channels therebetween. The open spaces between the ligaments form a matrix of continuous channels having few or no dead ends, such that growth of soft tissue and/or bone through open porous metal is substantially uninhibited. Thus, the open porous metal may provide a lightweight, strong porous structure which is substantially uniform and consistent in composition, and provides a matrix (e.g., closely resembling the structure of natural cancellous bone) into which soft tissue and bone may grow to provide fixation of the implant to surrounding bodily structures. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart and enhanced affixation ability to an exposed porous metal surface for adhering to bone and soft tissue. Also, when such highly porous metal structures are coupled to an underlying substrate, a small percentage of the substrate may be in direct contact with the ligaments of the highly porous structure, for example, approximately 15%, 20%, or 25%, of the surface area of the substrate may be in direct contact with the ligaments of the highly porous structure.

An open porous metal structure may also be fabricated such that it comprises a variety of densities in order to selectively tailor the structure for particular orthopedic applications. In particular, as discussed in the above-incorporated U.S. Pat. No. 5,282,861, an open porous metal structure may be fabricated to virtually any desired density, porosity, and pore size (e.g., pore diameter), and can thus be matched with the surrounding natural tissue in order to provide an improved matrix for tissue ingrowth and mineralization. According to certain examples, an open porous metal structure may be fabricated to have a substantially uniform porosity, density, and/or void (pore) size throughout, or to comprise at least one of pore size, porosity, and/or density being varied within the structure. For example, an open porous metal structure may have a different pore size and/or porosity at different regions, layers, and surfaces of the structure. The ability to selectively tailor the structural properties of the open porous metal, for example, enables tailoring of the structure for distributing stress loads throughout the surrounding tissue and promoting specific tissue ingrown within the open porous metal.

In other examples, an open porous metal structure may comprise an open cell polyurethane foam substrate coated with Ti-6Al-4V alloy using a low temperature arc vapor deposition process. Ti-6Al-4V beads may then be sintered to the surface of the Ti-6Al-4V-coated polyurethane foam substrate. Additionally, another example of an open porous metal structure may comprise a metal substrate combined with a Ti-6Al-4V powder and a ceramic material, which is sintered under heat and pressure. The ceramic particles may thereafter be removed leaving voids, or pores, in the substrate. An open porous metal structure may also comprise a Ti-6Al-4V powder which has been suspended in a liquid and infiltrated and coated on the surface of a polyurethane substrate. The Ti-6Al-4V coating may then be sintered to form a porous metal structure mimicking the polyurethane foam substrate. Further, another example of an open porous metal structure may comprise a porous metal substrate having particles, comprising altered geometries, which are sintered to a plurality of outer layers of the metal substrate. Additionally, an open porous metal structure may be fabricated according to electron beam melting (EBM) and/or laser engineered net shaping (LENS). For example, with EBM, metallic layers (comprising one or more of the biomaterials, alloys, and substrates disclosed herein) may be coated (layer by layer) on an open cell substrate using an electron beam in a vacuum. Similarly, with LENS, metallic powder (such as a titanium powder, for example) may be deposited and coated on an open cell substrate by creating a molten pool (from a metallic powder) using a focused, high-powered laser beam.

Because the sheet 102 can be formed of a porous structure, like the above-described porous tantalum, the sheet 102 can promote bone ingrowth and fusion in some circumstances, as described further below.

Figure 2:
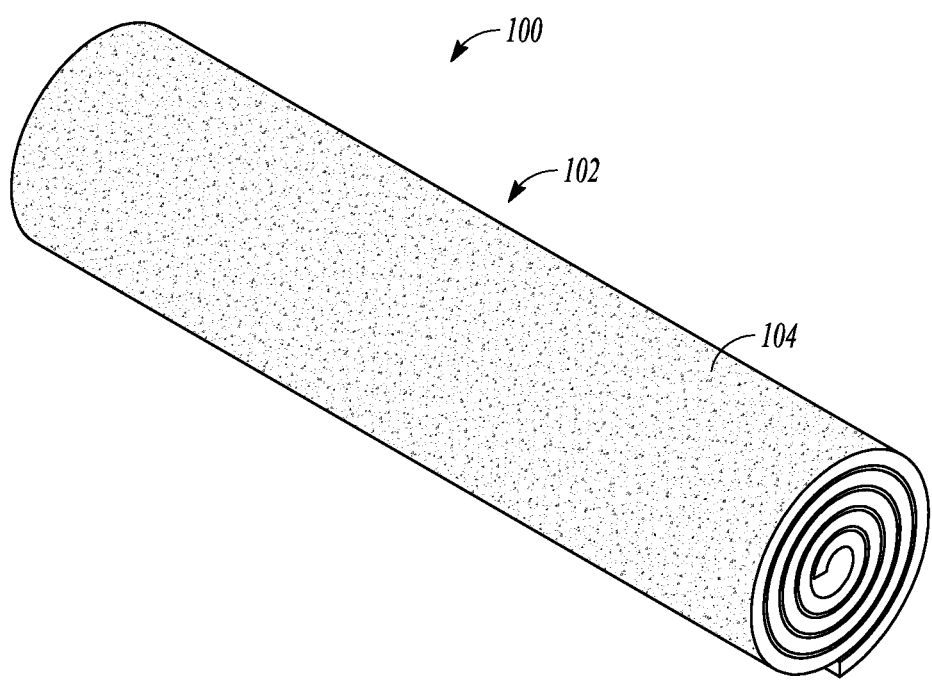
FIG. 2 is a perspective view of the shapeable porous implant of FIGS. 1A and 1B, rolled over itself for delivery to a patient.

FIG. 2 illustrates that in some cases the sheet 102 can be shaped as a roll or other shape to better facilitate delivery of the shapeable porous implant 100 to a surgical site. Thus, the thickness of the sheet 102 allows the shapeable porous implant 100 to be temporarily deformed (rolled, etc.) to decrease the delivery profile of the sheet. Deformation of the shapeable porous implant 100 prior to and/or during delivery can facilitate smaller less invasive access paths to the target area allowing for quicker patient recovery among other benefits. After delivery, the sheet 102 can be unrolled or otherwise shaped within the patient (e.g., reshaped from the delivery shape to an implant shape).

Figure 3:
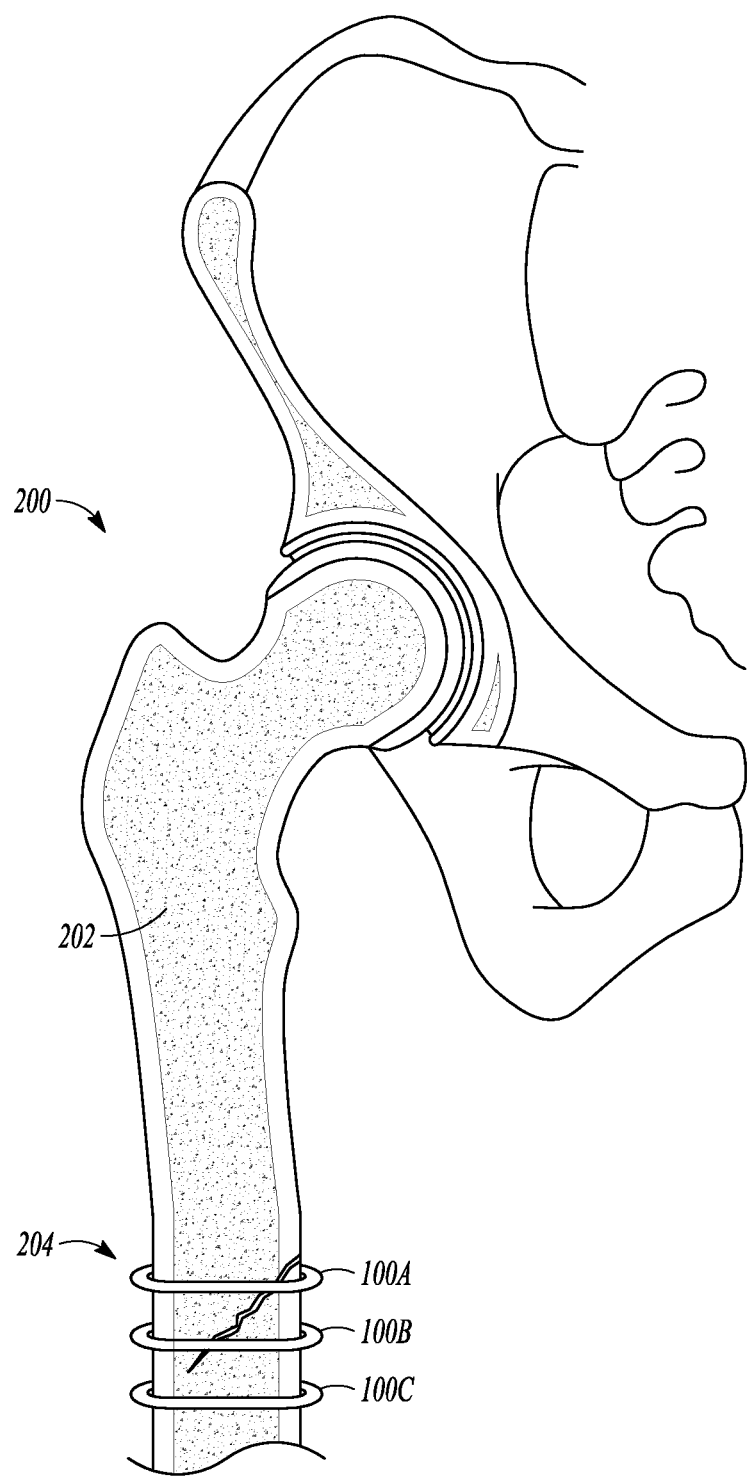
FIG. 3 is view of a patient's femur having a bone fracture treated by a plurality of shapeable porous implants according to an example of the present application.

FIG. 3 shows a partial cross section of a patient's anatomy 200 including a femur 202 that has sustained a long bone fracture at site 204. Examples of shapeable porous implants 100a, 100b, and 100c are disposed adjacent the site 204 in a target area along the femur 202. The shapeable porous implants 100a, 100b, and 100c can wrap circumferentially around the femur 202 (e.g., wrap circumferentially around at least one bone). According to the examples illustrated, the shapeable porous implants 100a, 100b, and 100c can comprise elongated strands having circular cross-sections with a diameter of between about 0.02 inch to 0.07 inch. Such strands or other elongate elements can have any suitable cross-sectional shape. The porous implants 100a, 100b, and 100c are disposed to interface with multiple sides of the site to aid in the retention of bone fragments and/or to aid in directing bone growth. In FIG. 3, the porous implants 100a, 100b, and 100c can be shaped to provide rings that can surround the site 204 by substantially 360° and even overlap with themselves in some instances. Although illustrated as cylindrical rings in FIG. 3, the shapeable porous implants 100a, 100b, and 100c can have various shapes as desired. For example, they can be sheets similar to the sheets of FIGS. 1A-2 formed around the site 204. Although three shapeable porous implants are illustrated spaced apart in FIG. 3, in some cases only a single implant or multiple overlapping implants can be utilized as desired.

Figure 4:
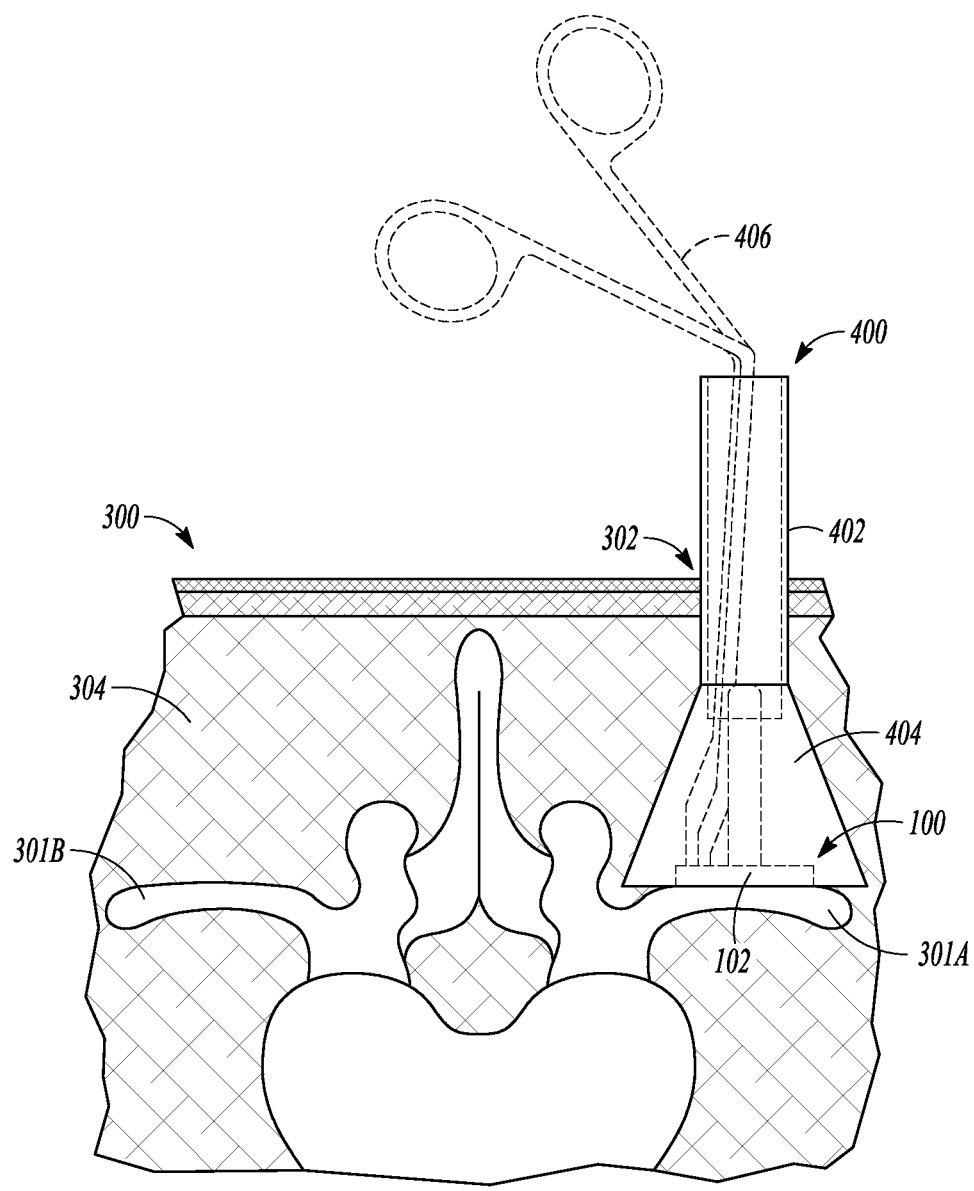
FIG. 4 is a schematic sectional view of a surgical cannula delivering the shapeable porous implant of FIGS. 1A-2 during a posterolateral fusion procedure.

FIG. 4 is a cross-sectional view of a portion of a patient's anatomy 300 including a posterior view of a portion of the spine surrounded by soft tissue 304. In FIG. 4, the patient is undergoing a posterolateral fusion procedure for which a path 302 has been formed in the soft tissue 304 allowing access by a surgical instrument 400 to a site along the transverse process 301a.

FIG. 4 illustrates an example where the surgical instrument 400 comprises a cannula with a tubular portion 402 and an expandable portion 404. Further details regarding the structure and function of the cannula can be found in co-owned U.S. Pat. Nos. 6,837,891, 7,001,397, 7,033,369, 7,108,705, 7,223,278, 7,670,354, 7,674,273, 7,892,171, 7,892,249, 7,985,237, 8,317,817, and 8,540,746, which are incorporated herein by reference. The cannula allows access by surgical instruments 406 to the target area.

In FIG. 4, the target area can be along the transverse processes 301a and 301b of the patient. FIG. 4 illustrates the porous implant 100 comprising the sheet 102 positioned in contact with the transverse process 301a but not yet disposed along the transverse process 301b. The shapeable porous implant 100 can be delivered to the site as a roll (as illustrated in FIG. 2) and then unrolled and wrapped and optionally molded or otherwise shaped to the transverse process 301a. In some instances such as the instance illustrated in FIG. 4, the porous implant 100 can be disposed outside the path 302 due to expansion (e.g. unrolling, shaping, molding etc.) of the porous implant 100.

Figure 5:
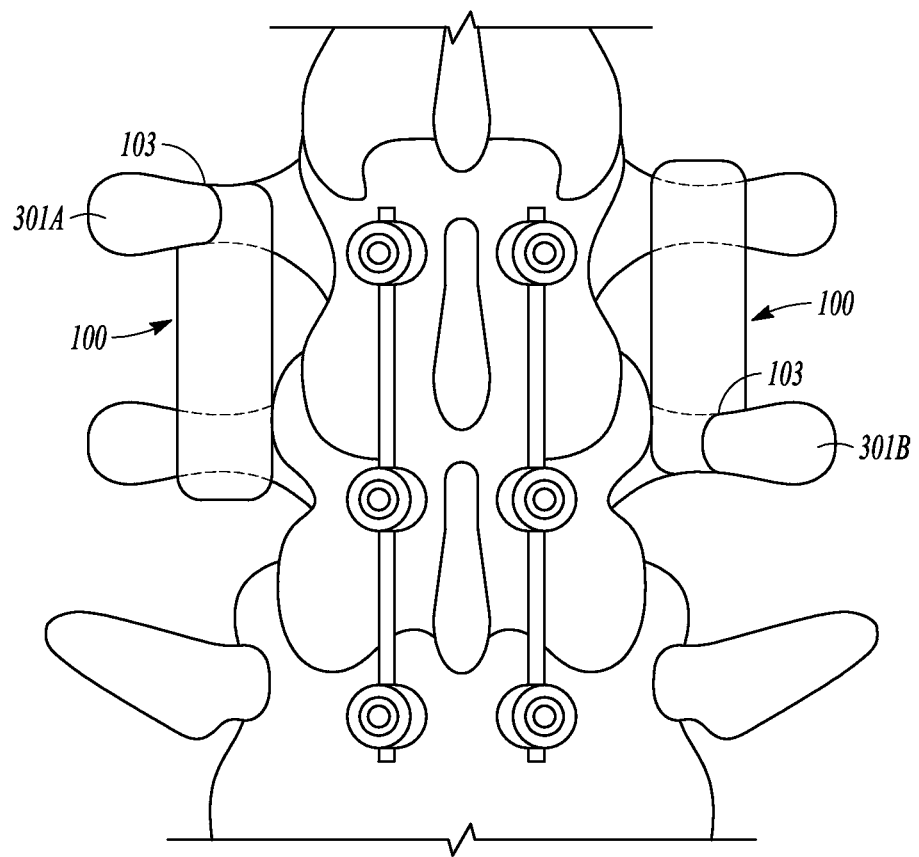
FIG. 5 is a schematic view of a portion of a spine having undergone the posterolateral fusion procedure with shapeable porous implants positioned in contact with the transverse processes.

FIG. 5 shows the anatomy 300 including a portion of a spine having undergone the posterolateral fusion procedure with the shapeable porous implants 100 comprising sheets positioned in contact with the transverse processes 301a and 301b and extending to adjacent transverse processes in the anterior/posterior direction. Thus, the shapeable porous implants 100 can be positioned in contact with a first bone and a second bone. In further instances, the shapeable porous implants 100 can be positioned to facilitate fusion across a joint (e.g. arthrodesis of a joint in a toe, ankle, finger, etc.).

As illustrated in FIG. 5, edge features 103 can aid in connecting the porous implants 100 to bone. Additionally, the porous implants 100 can be circumferentially wrapped and otherwise shaped to the anatomy (e.g., the transverse processes 301a and 301b). In some circumstances, techniques to secure the porous implants 100 to the anatomy can be utilized including bone cement, fasteners, and surface features (e.g., hooks, tabs, barbs, holes, slots, etc.). The porous implants 100 can act as a fusion aid to promote bone fusion. In some instances, the porous implants 100 can act as a bone grafting platform to which one or more bone grafts (FIG. 6) can be anchored. Additionally, the porous implants 100 can act as a structure for bone graft containment in some circumstances.

Figure 6:
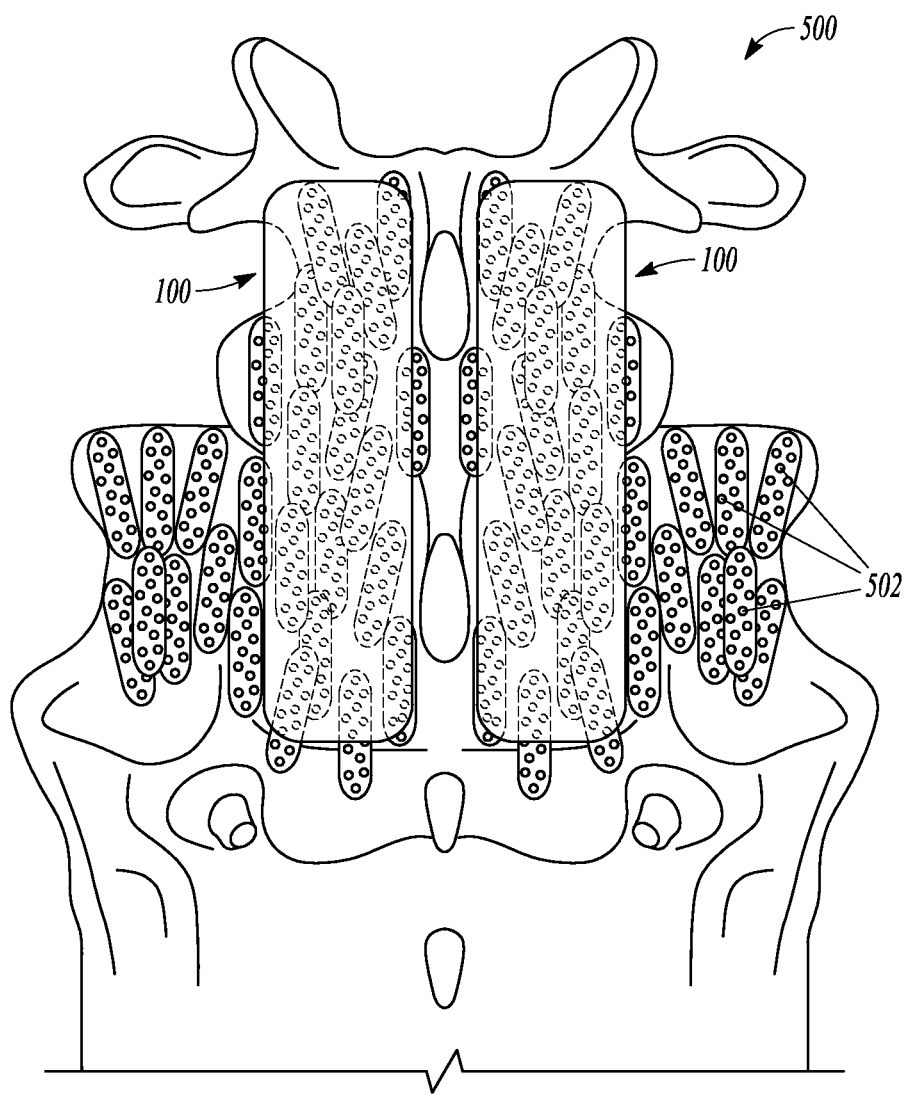
FIG. 6 is a schematic view of a portion of a spine having undergone a posterolateral gutter fusion procedure with shapeable porous implants positioned in contact with a plurality of bone grafts.

FIG. 6 illustrates an anatomy 500 comprising a portion of a spine from the L4 to S1 having undergone a posterolateral gutter fusion procedure. Shapeable porous implants 100 can be positioned to contact and affix to a plurality of bone grafts 502 and the gutters to the medial and lateral sides. The shapeable porous implants 100 can be molded intra-operatively to take on a shape that conforms to the gutters. Additionally, the shapeable porous implants 100 can serve as a bone grafting platform to which the plurality of bone grafts 502 can be attached. The molding of the porous implants 100 can take place in vivo and/or ex vivo as desired. In further instances, the porous implants 100 can act as a structure for bone graft containment and/or as a fusion aid in some circumstances.

The present application discloses various exemplary methods of treatment including for spinal fusion and long bone fracture. It should be understood that the shapeable porous implants can be used in further treatments such as maxiofacial reconstruction, arthrodesis of various joints, etc. not specifically illustrated. Indeed, the present application contemplates the use of the techniques, devices, systems, and methods disclosed herein for treatments where an injury has not occurred but the risk of a bone injury is present due to osteoporosis and other forms of bone degeneration. In further examples, the shapeable porous implant(s) can be used with and attached to additional implantable devices using known techniques. For example, the porous implant can be attached to a biocompatible metal such as a titanium or titanium alloy using known techniques for bonding or attaching. U.S. Pat. No. 7,918,382, entitled "METHOD FOR ATTACHING A POROUS METAL LAYER TO A METAL SUBSTRATE", directed to a method for attaching a porous metal structure to a metal substrate for forming orthopedic implants; and U.S. Pat. No. 8,608,049, entitled "METHOD FOR BONDING A TANTALUM STRUCTURE TO A COBALT-ALLOY SUBSTRATE", directed to a method for bonding a porous tantalum structure to a substrate comprising cobalt or a cobalt-chromium alloy the disclosures of which are incorporated herein by reference. Reference is also made to U.S. Published Application No. 2012/0125896, entitled "RESISTANCE WELDING A POROUS METAL LAYER TO A METAL SUBSTRATE", and directed to an apparatus and method for manufacturing an orthopedic prosthesis by resistance welding a porous metal layer to a metal substrate of the orthopedic prosthesis.

The present application can include a method of providing support to bone. The method can further include providing a sheet of highly porous metal material having a porosity of between 55% and 90% for encouraging bone ingrowth into said sheet and wrapping the sheet of highly porous metal material around at least a first bone of the patient. In further examples, the method can form the porous metal sheet intra-operatively to a desired shape to match an anatomy of the patient. The method can further include providing the sheet with a thickness of between about 0.02 inch to 0.07 inch and introducing the sheet to a surgical site as a roll. In a further example, the method wraps around a second bone for fusing the first bone to the second bone. In yet further examples, the method can treat one or more of a long bone fracture, a spinal injury, and a maxiofacial injury.

The present application can include an orthopedic implant. The implant can comprise an implantable sheet having a first face opposite a second face at least one of the first and second face comprising tissue interfacing surface. The sheet can be formed of a highly porous metal material having a porosity of between 55% and 90%. The tissue interface surface can include one or more features configured to facilitate retention of the sheet to an anatomy of a patient. According to a further example, the sheet can have a thickness of between about 0.02 inch to 0.07 inch and is configured to allow the sheet to be molded intra-operatively to a desired shape to match the anatomy of the patient. In yet further examples, a surgical instrument can be adapted to receive the sheet as a roll for delivery to the patient. The porous metal comprises a tantalum or tantalum alloy. The sheet can be molded to at least one bone for treatment of one or more of a long bone fracture, a spinal injury, and a maxiofacial injury. The one or more features can comprise one or more of surface features and edge features. The one or more features can comprise one or more of hooks, tabs, barbs, holes, and slots.

The present application can include a system for treating a patient with a shapeable implant. The system can include a sheet of porous metal and a surgical instrument. The porous metal sheet can have at least one tissue interfacing surface and a thickness of between about 0.02 inch to 0.07 inch and is configured to allow the sheet to be molded intra-operatively to a desired shape to match an anatomy of the patient. The surgical instrument can be configured to deliver the sheet to a target area within the patient for implantation and molding to the desired shape.

In an example, the surgical instrument can comprise a cannula adapted to receive the sheet as a roll. In a further example, the porous metal can comprise a tantalum or tantalum alloy. In yet a further example, molding to the desired shape occurs in vivo upon implantation. The sheet can be molded for treatment of one or more of a long bone fracture, a spinal injury, and a maxiofacial injury. The sheet can have one or more features that are configured to facilitate retention of the porous metal implant to the anatomy of the patient.

The present application can additionally include a method of fusing at least a first bone to a second bone. The method can include providing a sheet of highly porous metal material having a porosity of between 55% and 90%, and positioning the sheet in contact with the first bone and the second bone for fusing the first bone to the second bone of a patient. Further examples of the method can mold the sheet intra-operatively to a desired shape to match an anatomy of the patient. The method can additionally wrap the sheet around at least the first bone of the patient. Further examples fully surround the site by substantially 360° with the wrap. In further examples, the first bone and the second bone can comprise bones of the vertebrae of the patient. Additionally, the method can have the sheet fuse across a joint of the patient.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An orthopedic implant, comprising:
an implantable sheet having a first face opposite a second face, at least one of the first face and the second face comprising a tissue interfacing surface, the sheet formed of a highly porous metal material having a porosity of between 55% and 90%, wherein the tissue interfacing surface includes at least one of a tab, a hook or a barb extending therefrom, the at least one of the tab, the hook or the barb configured to couple with bone or soft tissue of a patient to facilitate retention of the sheet to the bone or the soft tissue upon initial implantation of the sheet into the patient.

2. The implant of claim 1, wherein the sheet has a thickness of between about 0.02 inch and about 0.07 inch and is configured to allow the sheet to be molded intra-operatively to a desired shape.

3. The implant of claim 1, in combination with a surgical instrument adapted to receive the sheet as a roll for delivery to the patient.

4. The implant of claim 1, wherein the porous metal material comprises a tantalum or tantalum alloy.

5. The implant of claim 1, wherein the sheet is moldable to at least one bone for treatment of one or more of a long bone fracture, a spinal injury, and a maxiofacial injury.

6. The implant of claim 1, wherein the one or more features comprise a surface feature and/or an edge feature.

7. An orthopedic implant, comprising:

an implantable sheet having a first face opposite a second face, at least one of the first face and the second face comprising a tissue interfacing surface, the sheet formed of a highly porous metal material having a porosity of between 55% and 90%, wherein the tissue interfacing surface includes a surface feature comprising one or more of a tab, a hook, or a barb extending therefrom and configured to couple with a first anatomy of a patient and an edge feature comprising a slot with an opening along an edge of the sheet, the slot configured to couple with a second anatomy of the patient to facilitate retention of the sheet to the first anatomy and the second anatomy upon initial implantation of the sheet into the patient.

8. The implant of claim 7, wherein the sheet has a thickness of between about 0.02 inch and about 0.07 inch and is configured to allow the sheet to be molded intraoperatively to a desired shape.

9. The implant of claim 7, in combination with a surgical instrument adapted to receive the sheet as a roll for delivery to the patient.

10. The implant of claim 7, wherein the porous metal material comprises a tantalum or tantalum alloy.

11. The implant of claim 7, wherein the sheet is moldable to at least one bone for treatment of one or more of a long bone fracture, a spinal injury, and a maxiofacial injury.

12. An orthopedic implant, comprising:

an implantable sheet having a first face opposite a second face, at least one of the first face and the second face comprising a tissue interfacing surface, the sheet formed of a highly porous metal material having a porosity of between 55% and 90%, wherein the tissue interfacing surface includes an edge feature comprising a slot with an opening along an edge of the sheet the slot communicating with a hole defined in part by the tissue interfacing surface that passes through the implantable sheet, together the slot and the hole are configured to receive bone or soft tissue therein to facilitate retention of the sheet to the bone or the soft tissue upon initial implantation of the sheet into a patient.

13. The implant of claim 12, wherein the sheet has a thickness of between about 0.02 inch and about 0.07 inch and is configured to allow the sheet to be molded intraoperatively to a desired shape.

14. The implant of claim 12, in combination with a surgical instrument adapted to receive the sheet as a roll for delivery to the patient.

15. The implant of claim 12, wherein the porous metal material comprises a tantalum or tantalum alloy.

16. The implant of claim 12, wherein the sheet is moldable to at least one bone for treatment of one or more of a long bone fracture, a spinal injury, and a maxiofacial injury.

17. The implant of claim 12, wherein the surface additionally includes a surface feature.

* * * * *